(12) United States Patent
Yarmut

(10) Patent No.: US 6,576,257 B1
(45) Date of Patent: Jun. 10, 2003

(54) TARGETED DRUG ACTIVATION

(76) Inventor: Yehuda Yarmut, Givat Hamigdal Street, P.O. Box 140, 20 600 Moshava Yokneam (IL)

( * ) Notice: Subject to any disclaimer, the term of this patent is extended or adjusted under 35 U.S.C. 154(b) by 0 days.

(21) Appl. No.: 10/110,038

(22) PCT Filed: Oct. 10, 2000

(86) PCT No.: PCT/IL00/00637

§ 371 (c)(1),
(2), (4) Date: Apr. 8, 2002

(87) PCT Pub. No.: WO01/26704

PCT Pub. Date: Apr. 19, 2001

Related U.S. Application Data

(60) Provisional application No. 60/158,383, filed on Oct. 12, 1999.

(51) Int. Cl.[7] .............................. A61K 9/48; A61K 9/14; A61K 9/127
(52) U.S. Cl. .................. 424/451; 424/489; 424/450
(58) Field of Search .................. 424/451, 489, 424/450

(56) References Cited

U.S. PATENT DOCUMENTS

| | | | |
|---|---|---|---|
| 5,190,761 A | | 3/1993 | Liburdy |
| 5,542,935 A | | 8/1996 | Unger et al. |
| 5,780,044 A | | 7/1998 | Yewey et al. |
| 5,820,879 A | | 10/1998 | Fernandez et al. |
| 6,028,066 A | * | 2/2000 | Unger .................. 514/180 |
| 6,099,864 A | * | 8/2000 | Morrison et al. ......... 424/489 |

* cited by examiner

*Primary Examiner*—Thurman K. Page
*Assistant Examiner*—Blessing Fubara
(74) *Attorney, Agent, or Firm*—G. E. Ehrlich Ltd.

(57) ABSTRACT

A method of providing a drug to a specific region of a patient's body is provided. The method includes the steps of: (a) administering to the patient a prodrug being convertible to the drug upon exposure to a predetermined dose of energy; and (b) irradiating the specific region of the body with at least two energy waves, each being provided from a different direction and/or distance, thereby generating the predetermined dose of energy in the specific region of the body and converting the prodrug into the drug therein.

42 Claims, 1 Drawing Sheet

TARGETED DRUG ACTIVATION

This application is a 371 of PCT/IL 00/00637 filed Oct. 10, 2000 which claims benefit of provisional application 60/158,383 filed Oct. 12, 1999.

FIELD AND BACKGROUND OF THE INVENTION

The present invention relates to a targeted drug activation method and more particularly, to body region specific drug activation enabled via focused energy provided from at least two energy waves, such as, for example, ultrasound and shock waves.

The conventional methods of drug administration are the oral ingestion of tablets, capsules, liquid drug formulations, etc.; parenteral administration into the blood stream or tissues; and rectal suppository administration. Such methods are far from ideal, since they provide wide variations in plasma concentration of drugs at different times between dosages, ranging from ineffectively low concentrations to toxic levels at which harmful side effects can be experienced.

Moreover, such methods are essentially non-site specific, and deliver the drug to substantially all parts of the body and all body organs, not just the regions needing treatment by the drug. Such unfocused drug delivery subjects various body parts and organs to unneeded and oftentimes toxic substances and as such it can lead to unwanted side effects.

It has been well recognized in the medical field that one of the most effective ways to treat diseased tissues is to direct the drug treatment to the diseased area only. One particular form of drug therapy where localized action of the drug is important is cancer therapy. Drugs which are effective in attacking malignant cells, to limit their proliferation, have a tendency to attack benign cells as well, so that it is highly desirable to limit the location of their action to that of the malignancy, and to ensure that effective, but not excessive, amounts of such drugs are used, at any particular time, and further that other body-parts will not be affected by the drug.

Attempts to administer such drugs by direct injection into the location or organ having the malignancy are only partially effective. Oftentimes the malignant cells which can comprise a small fraction of a tumor mass reside deep within the tumor mass and as a result are poorly vascularized. Due to their scarcity and poor vascularization these cells are poorly targeted by a drug administered via a direct injection. Furthermore, diffusion and/or leakage of the drug from the injection site can also occur. As a result, the above limitations of direct drug injections dictate the administration of excessive quantities of the drug to effect treatment.

More effective methods for targeting drug release involve the use of prodrugs. A Prodrug constitutes a pharmaceutically inert compound or composition formed from a drug complexed with or formed within various biological carriers such as biopolymers. As such, the drug forming the prodrug can be released from the carrier by various mechanisms employed in or by selected body tissues to effect treatment.

The use of prodrugs in targeted drug therapy has been achieved to some extent by packaging or complexing the drug with biodegradable polymers or other molecules which can be placed at specific locations in the body and to effect a sustained/retarded release. In some cases slow release can be initiated by specific diseased body tissues which are characterized by distinct physiological environments typified by having a distinct pH or macromolecular content.

Although some targeting of drugs via a controlled and timed release packaging can be effected, this method is still very limited in its targeting capabilities.

A more accurate and versatile method to direct and target drugs within the body is described in U.S. Pat. Nos. 4,801, 459 and 5,190,761 and involves the application of directed electromagnetic radiation such as microwave or ultrasound for disrupting drug containing capsules, such as liposomes, in a specific area of the patient's body and as such to effect a localized release of the drug from the capsules.

Accordingly, other similar methods, which employ laser radiation, infrared radiation or ultrasound radiation to activate release from a drug carrying liposome have also been described (see U.S. Pat. Nos. 4,891,043; 5,470,582 and 4,898,734).

Photodynamic therapy (PDT), is another drug activation approach in which a light source, such as a laser is used for transforming an inactive photosensitive molecule into a free radical (see for example, U.S. Pat. Nos. 5,257,970; 4,649, 151; 4,866,168 and 4,889,129).

Although the above described drug targeting methods improve drug targeting efficiency as compared to standard drug delivery methods, they still suffer from inherent limitations.

These prior art methods employ a single energy wave for drug activation and as such, the portion of the body through which the energy wave travels is exposed to a dose of energy sufficient for activating the drug. This exposes portions of the body which are not to be treated to the possible adverse effects of the drug. Thus, the use of such methods for targeting the release of cytotoxic drugs at small tumors is a virtual impossibility. This is especially true for liposome carrying drugs which are administered systematically. Due to the inherent instability of liposomes, an "unfocused" energy dose can activate release from a liposome carrying drug in a large portion of the patients body or in a major blood vessel, thus leading to a dispersed drug release and in the case of cytotoxic drugs, to severe side effects.

Furthermore, in cases where drug activation is effected by exposure to large doses of energy, such "unfocused" activation can lead to damage in regions of the body which are not to be treated.

There is thus a widely recognized need for, and it would be highly advantageous to have, a method for targeted drug activation devoid of the above limitation.

SUMMARY OF THE INVENTION

According to the present invention there is provided a method of providing a drug to a specific region of a patient's body, the method comprising the steps of: (a) administering to the patient a prodrug being convertible to the drug upon exposure to a predetermined dose of energy; and (b) irradiating the specific region of the body with at least two energy waves, each being provided from a different direction, thereby generating the predetermined dose of energy in the specific region of the body and converting the prodrug into the drug therein.

According to still another aspect of the present invention there is provided a method of treating a tumor in a specific region of a human body comprising the steps of: (a) administering to the patient a prodrug being convertible to a drug having cytotoxic activity upon exposure to a predetermined dose of energy; and (b) irradiating the specific region of the body with at least two energy waves, each being provided from a different direction, thereby generating the predetermined dose of energy in the specific region of the body and converting the prodrug into the drug therein.

According to further features in preferred embodiments of the invention described below, the drug is selected from the group consisting of fluorouracil, cisplatinum, vinblastin, an anthracycline analogue and doxorubicin.

According to further features in the described preferred embodiments the at least two energy waves converge upon the specific region of the body.

According to still further features in the described preferred embodiments the at least two energy waves cross one another at a location within the specific region of the body.

According to still further features in the described preferred embodiments the specific region of the body is sequentially irradiated with the at least two energy waves.

According to still further features in the described preferred embodiments the specific region of the body is simultaneously irradiated with the at least two energy waves.

According to still further features in the described preferred embodiments each of the at least two energy waves delivers an energy dose to the specific region of the body which is below the predetermined dose of energy required for converting the prodrug into the drug.

According to still further features in the described preferred embodiments each of the at least two energy waves is of a specific wavelength.

According to still further features in the described preferred embodiments the at least two energy waves are of identical wavelengths.

According to still further features in the described preferred embodiments the prodrug is a microsphere encapsulated drug.

According to still further features in the described preferred embodiments the microsphere also contain a radio-contrast media.

According to still further features in the described preferred embodiments the prodrug is solubilized in liposomes.

According to still further features in the described preferred embodiments the liposomes also contain radio contrast media.

According to still further features in the described preferred embodiments the prodrug is a micelle bound drug.

According to still further features in the described preferred embodiments the drug is bound to the outside surface of the micelle.

According to still further features in the described preferred embodiments the prodrug is a gas filled microcapsule encapsulated drug.

According to still further features in the described preferred embodiments the prodrug includes at least one labile chemical bond.

According to still further features in the described preferred embodiments the predetermined energy dose cleaves the at least one labile bond thereby converting the prodrug into the drug.

According to still further features in the described preferred embodiments the drug is selected from the group consisting of a hormone, an enzyme, a DNA construct, an antibody and a vaccine.

According to still further features in the described preferred embodiments the drug is selected from the group consisting of an anti-cancer drug, an anti-inflammatory drug, a cardiac active drug and a CNS active drug.

According to still further features in the described preferred embodiments each of the at least two distinct energy waves is independently selected from the group consisting of laser energy waves, ultra-sound and shock energy waves, ultra-violet energy waves, infrared and near infrared light, magnetic energy waves, radiofrequency energy waves and microwave energy waves.

The present invention successfully addresses the shortcomings of the presently known configurations by providing a method of targeted drug release which can be utilized to treat preselected regions within a patients body.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
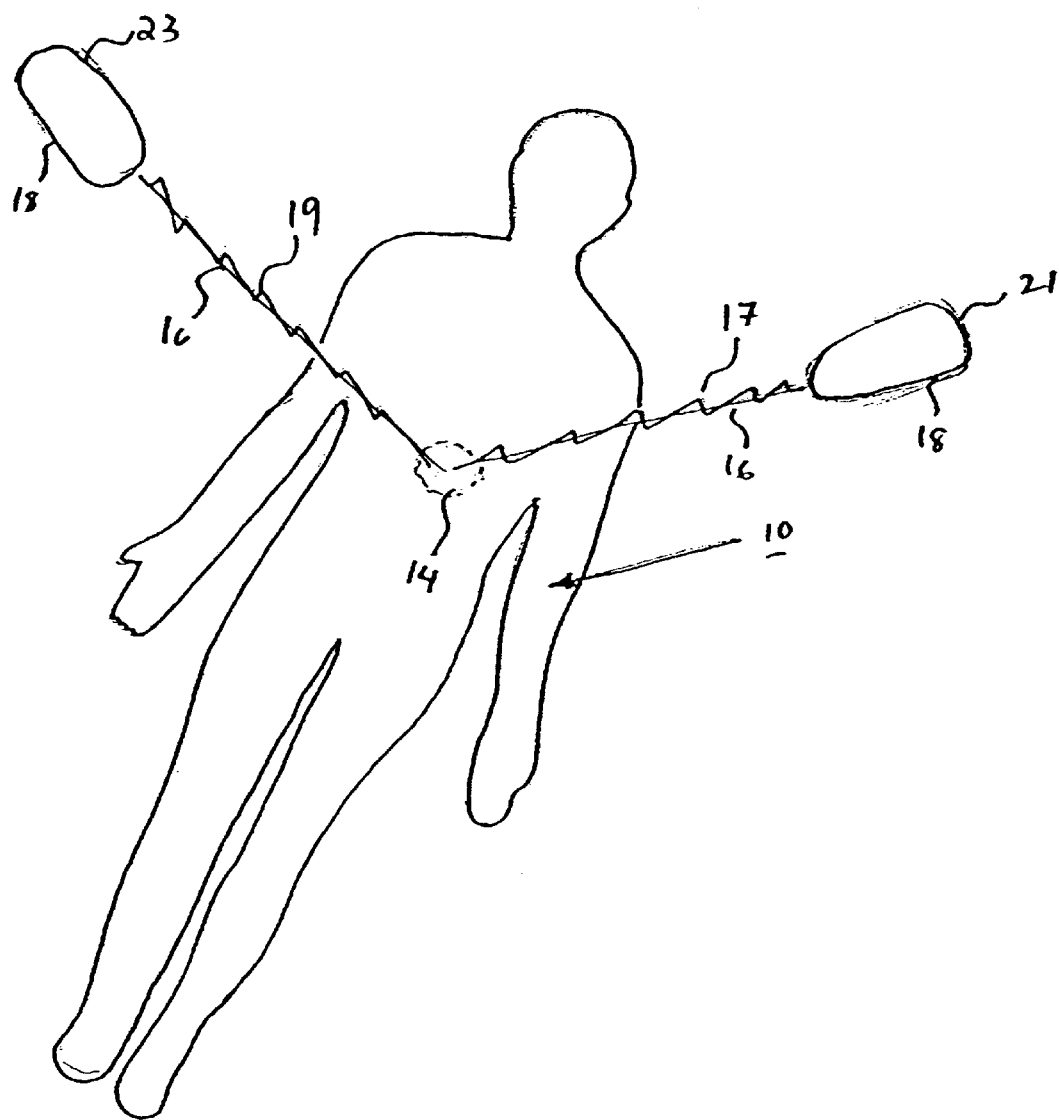
FIG. 1 is a schematic diagram depicting targeted drug release according to the teachings of the present invention.

The present invention is of a targeted drug release method which can be used to treat a preselected region of a patient's body. More specifically, the present invention can be utilized to treat diseased tissues, such as for example, tumor tissues, by activating cytotoxic drug activity within such tissue via a focused energy dose.

The principles and operation of a composition and method for therapy of a preselected portion of a patient's body according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 illustrates the method of providing a drug to a specific region of a patient's body according to the present invention.

The method is effected by first administering to the patient a predetermined dose of a prodrug, via any one of several administration modes known in the art. The mode of administration depends on the location and tissue type of the region to be treated. For example, for treating vascularized tumor tissue, the prodrug is administered via an intravenous injection, as indicated by 10, or via a direct injection.

As used herein, the term "prodrug" refers to a proactive form of a drug which is convertible into the drug only following absorption of a predetermined energy dose.

Examples of various prodrugs which can be utilized by the present invention are provided hereinunder. Prodrugs are often useful because many cytotoxic or bioactive drugs and enzymes cannot be injected intravenously. Others can be injected, but are rapidly degraded before they reach the target tissue. Still others are cleared from the blood by the liver or kidneys so quickly that their biological half-life is too short to be of therapeutic value. Still other drugs are insoluble in aqueous solutions. Since intravenous injection in hydrocarbon solvents is not well tolerated by patients, such drugs are difficult to administer. The use of a prodrug may also improved solubility in comparison to the parent drug in pharmaceutical compositions or may be less toxic than the parent drug.

Following administration of the prodrug, the specific region of the body to be treated (marked by 14) is irradiated by at least two energy waves 16, each being provided from a different direction and/or distance from an energy source 18. As is further described hereinunder such irradiation provides the predetermined energy dose necessary for converting the prodrug into the drug in the specific region of the body.

As used herein, the term "energy waves" refers to focused or dispersed (directed or non-directed) electro magnetic or sonic radiation such as, but not limited to, ultrasonic radiation, sonic radiation, such as shock waves, infrared and near infrared radiation, magnetic resonance radiation, X-ray radiation, radiofrequency radiation, laser radiation, and the like.

For example, ultrasound waves from two or more ultrasound transducers can be focused to provide the predetermined energy dose in a tissue volume of several cubic centimeters without causing damage to surrounding tissues. Similarly, shock waves, such as those utilized in Lithotripsy can also be safely utilized for activating a prodrug, such as a microsphere sequestered drug further described below.

Several approaches can be utilized in order to focus energy at a specific tissue region. For example, crossing or converging energy waves can be utilized to localize energy to a defined tissue region. Alternatively, a localized resonance effect of one energy wave on another can also be utilized for tissue specific energy provision.

Focusing energy at a specific tissue region via the use of two or more energy waves is well known in the art. For example, crossing or converging gamma radiation beams are utilized in the so called "gamma knife" procedure to treat small tissue regions (see for example, Goodman, South Med J. 1990 May;83(5):5514).

According to preferred embodiments of the present invention, energy waves 16 can be identical or different energy waves. For example, a first energy wave 17 can be provided, for example, via an ultrasound radiation source 21 whereas a second energy wave 19 can be provided, for example, via a magnetic resonance energy source 23.

Energy source(s) 18 (two are shown) are preferably positioned outside the patient's body. It will be appreciated however, that provision of such energy waves can also be effected from within the body, using for example, catheters provided with optic fibers or ultrasound transducers.

According to preferred embodiments of the present invention, the specific region of the body is sequentially or simultaneously irradiated with energy waves 16.

Irradiating the specific region of the body with at least two energy wave 16 each originating from a different direction provides substantial advantages over prior art methods.

As is mentioned in the background section above, prior art methods for drug activation utilize a single energy wave. As such, using such methods for region specific drug activation is oftentimes difficult since prodrug particles existing anywhere within the path traveled by the energy wave can also be activated.

The use of two (or more) energy waves 16 by the method of the present invention traverses this limitation since drug activation can occur only in a tissue region which is simultaneously or sequentially exposed to both energy waves.

Such "multi-directional" irradiation exposes the specific region of the body to an energy dose which is larger than that absorbed by the tissue forming the path traveled within the body by each energy wave. This enables activation of a prodrug having a predetermined activation energy at the specific region of the body in which the energy wave converge and/or cross.

It will be appreciated that in the case of sequential irradiation, the prodrug can be selected such that energy wave 17 converts the prodrug into an inactive intermediate, while energy wave 19 converts the inactive intermediate into the active form of the drug.

Preferably, sources 18 are placed near or on the patient's skin surface as close to the specific region of treatment. For example, if an intravenously administered prodrug is to be activated, the energy waves can be directed at the local circulation of the specific region such that prodrug molecules or particles circulating through this local vasculature are activated.

Several prodrug configurations can be utilized by the method of the present invention.

For example, the prodrug can be a microsphere or a microcapsule encapsulated drug which is released following absorption of the predetermined energy dose.

As used herein the terms "microsphere" and "microcapsule" refer to a microscopic storage vesicle.

The drug or precursors thereof can be incorporated, encapsulated, surrounded, or entrapped by, for example, lipid vesicles or liposomes, or by micelles.

The use of liposomes in generating prodrugs is well known in the art. Liposomes are a spherical-shaped bilayer structure composed of a natural or synthetic phospholipid membrane or membranes, and sometimes other membrane components such as cholesterol and protein, which act as a physical reservoir for drugs. These drugs may be sequestered in the liposome membrane or may be encapsulated in the aqueous interior of the vesicle. Liposomes are characterized according to size and to number of membrane bilayers vesicle diameter can be large (>200 nm) or small (<50 nm) and the bilayer can have a unilammellar, oligolammellar, or multilammellar membrane. The liposomes may include, for example, lipids such as cholesterol, phospholipids. Typically, the drugs bind to the lipid bilayer membrane of the liposome with high affinity and as such are released only following partial or complete disintegration of the liposome.

Liposomes have been used successfully to administer medications to cancer patients, and have been shown to be useful clinically in the delivery of anti-cancer drugs such as doxorubicin, daunorubicin, and cisplatinum complexes. Forssen, et al., Cancer Res. 1992, 52: 3255–3261; Perez-Soler, et al. Cancer Res. 1990, 50: 4260–4266; and, Khokhar, et al. J. Med Chem. 1991,34:325–329.

Similarly, micelles have also been used to deliver medications to patients, (Brodin et al., Acta Pharn. Suec. 19 267–284 (1982)) or used as drug carriers for targeted drug delivery, (D. D. Lasic, Nature 335: 279–280 (1992); and, Supersaxo et al., Pharm. Res. 8: 1286–1291 (1991); Fung et al., Biomater. Artif. Cells. Artif. Organs 16: 439 et. seq. (1988); and Yokoyama et al., Cancer Res. 51: 3229–3236 (1991)).

The predetermined energy dose delivered according to the teachings of the present invention disrupts the drug carrying microcapsules thus enabling drug release.

Alternatively such an energy dose enables drug precursors which are trapped within the microcapsule to mix and or react (for example, enzymatic reaction) and form the drug which can diffuse out of the microcapsule (for further detail see, for example, U.S. Pat. No. 6,099,864).

Another prodrug configuration which can be utilized by the present invention includes a first chemical moiety and a second chemical moiety which are inter-attached via a labile attachment, such as a covalent bond, to thereby form a prodrug. When the prodrug is subjected to the predetermined energy dose, such an attachment is disrupted causing the dissociation of the chemical moieties and activation of the drug.

A variety of labile attachments and configurations which can be utilized by the present invention are known in the art, see for example, U.S. Pat. No. 4,202,323 for further details.

It will be appreciated that such a prodrug configuration can include any number of labile attachments and/or moieties which when subjected to the predetermined energy dose can release one or more molecules which are active as drugs. For example, one can attach a first drug, such as a cytotoxic drug to a second drug, such as an anti-inflammatory drug, via one or more labile attachments to thereby form an inactive prodrug. Disassociation following irradiation would then release active forms of both drugs to the area of treatment. U.S. Provisional patent application No. 60/158,383 provides a detailed description of additional prodrug configuration which can be utilized by the present invention.

According to another preferred embodiment of the present invention, the method also includes the step of monitoring the location of the prodrug prior to or during activation.

This can be effected by including or attaching a contrast media, such as an isotope, to the prodrug so as to enable visualization via energy waves such as, ultrasound, x-ray, magnetic resonance and the like utilized for activation or dedicated to monitoring.

For example, the microcapsule configuration of the prodrug described above can include a contrast media, such as an oil, encapsulated along with the drug or attached to the surface thereof.

Alternatively, gas bubbles included within the microcapsules can serve as contrast media for ultrasound imaging methods for preparing gas filled liposomes are described in U.S. Pat. No. 5,935,553.

Thus, the present invention provides a method of targeted drug activation. Such a method can be utilized for local delivery of cytotoxic drugs capable of treating or eliminating a tumor or a pretumor, such as flurouracil or vinblastin; drugs that are active in the central nervous system (CNS) such as L-dopa or serotonin uptake inhibitors; bronchodilator drugs useful in treating lung spasms associated with cystic fibrosis and asthma; anti-spasmodics agents such as atropin or papverine as well as anti-parasitic agents that are targeted to the guts; local anasthetics; anti-microbial drugs; anti-inflammatory drugs and any drug utilized for treatment of localized disorders.

In certain embodiments, the prodrug is preferentially soluble in a hydrocarbon or oil phase and the active drug is preferentially soluble in an aqueous phase. Such embodiments would include, but are not limited to papaverine, which is activated to papaverine hydrochloride, which is useful as an antispasmodic in arterial smooth muscle; genoscopolamine, which is reduced to scopolamine; hematoporphyrin, activated to di-hematoporphyrin hematoporphyrin ester by weak acid; and quinidine, activated to quinidine hydrochloride or quinidine sulfate, useful as a treatment for auricular fibrillation.

The method of the present invention may be especially effective in treating tumors or cancer in a mammal.

As used herein, the terms "treating" or "treatment" refer to the ability to slow down, arrest or reverse the progression of a disease or disorder.

Since treatment of cancers and tumors involve the use of powerful cytotoxic drugs and agents, non-specific drug activation may lead to damage to healthy tissues, and in severe cases, death.

Since drug activation according to the teachings of the present invention can be effected in a tissue region which is several cubic centimeters in volume, microcapsule sequestered cytotoxins can be activated to release in a region defining even the smallest of detectable tumors.

Numerous prior art treatment protocols currently employ radiosensitizers activated by, for example, electromagnetic energy waves, such as X-rays.

Examples of x-ray activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Thus, the present invention provides a method of targeted drug activation. The use of two or more energy waves which are provided from different directions enables focused drug activation, while avoiding or minimizing the problems of tissue heating and drug activation in unwanted body regions which are associated with prior art activation methods.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications disclosed and mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

What is claimed is:

1. A method of providing a drug to a specific region of a patient's body, the method comprising the steps of:
   (a) administering to the patient a prodrug being convertible to the drug upon exposure to a predetermined dose of energy; and
   (b) irradiating the specific region of the body with at least two energy waves, each being provided from a different direction, thereby generating said predetermined dose of energy in the specific region of the body and converting said prodrug into the drug therein.

2. The method of claim 1, wherein said at least two energy waves converge upon the specific region of the body.

3. The method of claim 1, wherein said at least two energy waves cross one another at a location within the specific region of the body.

4. The method of claim 1, wherein the specific region of the body is sequentially irradiated with said at least two energy waves.

5. The method of claim 1, wherein the specific region of the body is simultaneously irradiated with said at least two energy waves.

6. The method of claim 1, wherein each of said at least two energy waves delivers an energy dose to the specific region of the body which is below said predetermined dose of energy required for converting said prodrug into the drug.

7. The method of claim 1, wherein each of said at least two energy waves is of a specific wavelength.

8. The method of claim 1, wherein said at least two energy waves are of identical wavelengths.

9. The method of claim 1, wherein said prodrug is a microsphere encapsulated drug.

10. The method of claim 9, wherein said microsphere also contain a radio-contrast media.

11. The method of claim 1, wherein said prodrug is solubilized in liposomes.

12. The method of claim 11, wherein said liposomes also contain radio contrast media.

13. The method of claim 1, wherein said prodrug is a micelle bound drug.

14. The method of claim 13, wherein the drug is bound to the outside surface of said micelle.

15. The method of claim 1, wherein said prodrug is a gas filled microcapsule encapsulated drug.

16. The method of claim 1, wherein said prodrug includes at least one labile chemical bond.

17. The method of claim 16, wherein said predetermined energy dose cleaves said at least one labile bond thereby converting said prodrug into the drug.

18. The method of claim 1, wherein the drug is selected from the group consisting of a hormone, an enzyme, a DNA construct, an antibody and a vaccine.

19. The method of claim 1, wherein said drug is selected from the group consisting of an anticancer drug, an anti-inflammatory drug, a cardiac active drug and a CNS active drug.

20. The method of claim 1, wherein each of said at least two distinct energy waves is independently selected from the group consisting of laser energy waves, shock waves, ultrasound energy waves, ultraviolet energy waves, infrared and near infrared light, magnetic energy waves, radiofrequency energy waves and microwave energy waves.

21. The method of claim 1, wherein said step of irradiating the specific region of the body with at least two energy waves is effected by at least one energy source positioned outside the patient's body.

22. The method of claim 1, further comprising the step of monitoring the specific region of the body for the presence of said prodrug prior to, or during, said step of irradiating.

23. A method of treating a tumor in a specific region of a patient's body comprising the steps of:

(a) administering to the patient a prodrug being convertible to a drug having cytotoxic activity upon exposure to a predetermined dose of energy; and (b) irradiating the specific region of the patient's body with at least two energy waves, each being provided from a different direction, thereby generating said predetermined dose of energy in the specific region of the patient's body and converting said prodrug into the drug therein.

24. The method of claim 23, wherein said drug is selected from the group consisting of fluorouracil, cisplatinum, vinblastin, an anthracycline analogue and doxorubicin.

25. The method of claim 23, wherein said at least two energy waves converge upon the specific region of the body.

26. The method of claim 23, wherein said at least two energy waves cross one another at a location within the specific region of the body.

27. The method of claim 23, wherein the specific region of the body is sequentially irradiated with said at least two energy waves.

28. The method of claim 23, wherein the specific region of the body is simultaneously irradiated with said at least two energy waves.

29. The method of claim 23, wherein each of said at least two energy waves delivers an energy dose to the specific region of the body which is below said predetermined dose of energy required for converting said prodrug into said drug.

30. The method of claim 23, wherein each of said at least two energy waves is of a specific wavelength.

31. The method of claim 23, wherein said at least two energy waves are of identical wavelengths.

32. The method of claim 23, wherein said prodrug is a microsphere encapsulated drug.

33. The method of claim 32, wherein said microsphere also contain a radio-contrast media.

34. The method of claim 23, wherein said prodrug is solubilized in liposomes.

35. The method of claim 34, wherein said liposomes also contain radio contrast media.

36. The method of claim 23, wherein said prodrug is a micelle bound drug.

37. The method of claim 36, wherein the drug is bound to the outside surface of said micelle.

38. The method of claim 23, wherein said prodrug is a gas filled microcapsule encapsulated drug.

39. The method of claim 23, wherein said prodrug includes at least one labile chemical bond.

40. The method of claim 39, wherein said predetermined energy dose cleaves said at least one labile bond thereby converting said prodrug into said drug.

41. The method of claim 23, wherein said step of irradiating the specific region of the body with at least two energy waves is effected by at least one energy source positioned outside the patient's body.

42. The method of claim 23, further comprising the step of monitoring the specific region of the body for the presence of said prodrug prior to, or during, said step of irradiating.

* * * * *